US008137664B2

(12) United States Patent
Nycz et al.

(10) Patent No.: US 8,137,664 B2
(45) Date of Patent: Mar. 20, 2012

(54) METHOD AND KIT FOR REPAIRING A DEFECT IN BONE

(75) Inventors: Jeffrey H. Nycz, Collierville, TN (US); Jon C. Serbousek, Memphis, TN (US)

(73) Assignee: SDGI Holdings, Inc., Wilmington, DE (US)

( * ) Notice: Subject to any disclaimer, the term of this patent is extended or adjusted under 35 U.S.C. 154(b) by 732 days.

(21) Appl. No.: 11/048,064

(22) Filed: Feb. 2, 2005

(65) Prior Publication Data

US 2006/0172934 A1  Aug. 3, 2006

(51) Int. Cl.
*A01N 63/00* (2006.01)
*A01N 43/04* (2006.01)
*A61N 48/00* (2006.01)
*A61K 31/715* (2006.01)

(52) U.S. Cl. ............... 424/93.2; 424/93.21; 514/44

(58) Field of Classification Search ............ 514/44; 424/93.1, 93.2, 93.21
See application file for complete search history.

(56) References Cited

U.S. PATENT DOCUMENTS

| | | | |
|---|---|---|---|
| 4,938,763 A | | 7/1990 | Dunn et al. |
| 5,278,201 A | | 1/1994 | Dunn et al. |
| 5,278,202 A | | 1/1994 | Dunn et al. |
| 5,744,153 A | | 4/1998 | Yewey et al. |
| 5,779,697 A | * | 7/1998 | Glowa et al. ............ 606/185 |
| 5,916,582 A | | 6/1999 | Stevenson et al. |
| 5,922,356 A | | 7/1999 | Koseki et al. |
| 5,932,547 A | | 8/1999 | Stevenson et al. |
| 5,954,635 A | * | 9/1999 | Foley et al. ............ 600/114 |
| 5,981,489 A | | 11/1999 | Stevenson et al. |
| 6,015,938 A | * | 1/2000 | Boyle et al. ............ 800/18 |
| 6,183,444 B1 | * | 2/2001 | Glines et al. ............ 604/187 |
| 7,371,408 B1 | * | 5/2008 | Petersen et al. ............ 424/549 |

OTHER PUBLICATIONS

Lee (Human Gene Therapy, Jul. 1, 2002, vol. 13, p. 1201-1211).*
Lee (J. Bone and Joint Surg., Jul. 2001, vol. 83A, No. 7, p. 1032-1039).*
Alden (Human Gene Therapy, 1999, vol. 10, p. 2245-2253).*
Alden (J. Neurosurgery (Spine 1), 1999, vol. 90, p. 109-114).*
Laurencin (Proceed. Int'l. Symp. Control. Rel. Bioact. Mater., 1997, vol. 24, abstract 220, p. 41-42).*
Abe (Biochem Biophysical Res. Commun., 2002, vol. 297, p. 523-527).*
Laurencin (Biomaterials, 2001, vol. 22, p. 1271-1277).*
Fang (PNAS, Jun. 1996, vol. 93, p. 5753-5738).*
Rose (Chirurgisches Forum fuer Experimentalle und Klinische Forschung, 2003, 5-8, abstract only).*
Pang (J. Periodontology, 2004, vol. 75, No. 10, p. 1364-1370, abstract only).*
Borden (J. Bone and Joint Surg., Nov. 2004, vol. 86, No. 8, p. 1200-1208).*
Sampath ("Bone morphogenetic protein (BMP) implants as bone graft substitutes", ASTM International, Cato T. Laurencin (ed.), Conshohocken, PA, 2003, p. 194-213).*
Erti (BioMedical Engineering OnLine, 2003, vol. 2, 15, p. 1-18).*
Ito (Nature Med. Mar. 2005, vol. 11, No. 3, p. 291-297).*
Winn (Orthod. Craniofacial Res., accepted Apr. 2005, vol. 8, p. 183-190).*
Wang (J. Bone and Joint Surgery, May 2003, vol. 85A, No. 5, p. 905-911).*
Bonadio (Nature Med., Jul. 1999, vol. 5, No. 7, p. 753-759).*
Kofron (Adv. Drug Delivery Rev., 2006, vol. 58, p. 555-576).*
Van de Belt (Acta Orthop. Scand., 2001, vol. 72, No. 6, p. 557-571).*
Tompkins (J. Bone and Joint Surgery, Feb. 1997, vol. 79, No. 2, p. 169-176.*
Maloney (J. Bone and Joint Surgery, Nov. 1997, vol. 79, No. 11, p. 1628-1634).*
Lavernia (J. Surg. Orthopaedic Advances, Fall 2004, vol. 13, No. 3, p. 174-176).*

* cited by examiner

*Primary Examiner* — Michael C. Wilson (57) ABSTRACT

Methods and devices are provided for the repair of bone defects. The bone defect repair may be accomplished by minimally invasive means. The bone defect repair may utilize a bone growth promoting substance. The bone growth promoting substance may comprise a carrier material and at least one osteoinductive formulation.

7 Claims, 5 Drawing Sheets

METHOD AND KIT FOR REPAIRING A DEFECT IN BONE

FIELD OF THE INVENTION

Embodiments of the invention relate to methods and kits for repairing a defect in bone. More specifically, the embodiments relate to open methods, and minimally invasive methods for treating bone defects using bone growth promoting substance comprising a carrier material and at least one bone growth promoting formulation.

DESCRIPTION OF RELATED ART

Orthopedic procedures for the replacement of all, or a portion, of a patient's joint have become common. These procedures are widely practiced and generally enjoy a high degree of success. Prosthetic hip and knee replacements comprise the majority of these procedures, however many other joints are also treated including, but not limited to, the shoulder, elbow, wrist, ankle, and temparomandibular joints.

Various conditions necessitate joint replacement. For example, hip replacements are performed to alleviate conditions caused by osteoarthritis, rheumatoid arthritis, fractures, dislocations, congenital deformities, and other hip-related conditions.

The hip joint includes articulation between a convex spherical ball (femoral head) and a concave socket (acetabular socket). Hip joint replacement consists of replacing the damaged articular surfaces with new articulating bearing surfaces. On the acetabluar side, a hemisphere-like cup is placed in the patient's damaged or worn socket, and fixed by some means to the patient's bone. On the femoral side, the prosthetic replacement consists of a sphere-like ball designed to fit into, and articulate with the prosthetic acetabular cup. The sphere-like ball may be a resurfacing device designed to fit over the patient's own femoral head (so called "surface replacement"). Or more commonly it consists of a ball attached to a stem, which is inserted into the femoral canal anchoring the prosthesis to the patient's femur. The ball and socket work as a pair in similar fashion to the original hip, restoring a partial range of linear and rotational motion.

Historically, acrylic-based cements were used to attach the prosthetic components to the respective portions of femur and pelvic bones. The area between the metal implant and the surrounding bone tissue was filled with acrylic cement. More recently, surgeons have begun using other techniques including biological fixation techniques such as direct osseointegration to metal or ceramic fixation surfaces and bone in growth into porous surfaces on implant surfaces. Preservation and maintenance of this secure fixation is critical to the long-term success of the prosthetic construct.

Whatever method is used to attach the prosthesis to the existing bone, the integrity of this interface is critical to the success of the artificial joint. Any weakening of the fixation between the bone and the prosthesis can lead to a loosening of the implant and movement relative to the bone. This loosening of the implant can lead a reduced range of motion and increased pain for the patient. Continuing loosening of the implant will eventually lead to failure of the artificial joint.

Osteolysis is a common problem that leads to the loosening of the bone/prosthesis interface, especially with regard to the acetabular cup/pelvic interface. As the articulated surfaces of the artificial joint move against each other, some particulate debris is generated. This particulate debris results from the wearing of one surface against the other and occurs to a greater or lesser extent regardless of the material used to form the articulating surfaces. The presence of this particulate debris causes a condition known as osteolysis. Osteolysis is generally defined as a type of particulate induced bone resorption, wherein the immune response of the patient causes the bone tissue surrounding the implant site to resorb away from the prosthetic component. Osteolysis can lead to aseptic loosening of the implant, and eventually, implant failure.

In accordance with the teachings of the prior art, osteolysis of the host bone with associated implant loosening and/or periprosthetic bone fracture requires major surgical intervention to remove the failed implants, reconstruct the damaged bone, and replace the failed prosthesis with a new artificial joint. This revision surgery is typically much more complicated than the initial implant surgery, and carries with it increased risks for perioperative complications, as well as increased risks for implant failure as compared to primary artificial joint replacement. Subsequent failures require further complex surgical intervention, with continually increasing risks of perioperative complications and early implant failure with each episode.

Osteolysis associated with orthopedic transplants is but one example of a bone defect. In addition to osteolysis, other bone defects such as voids, cracks, fissures, fractures, diseases, and other disorders often require invasive treatment.

The description herein of disadvantages and deleterious results achieved with known methods, instruments, devices, and compositions is in no way intended to limit the scope of the embodiments described herein to their exclusion. Indeed, various aspects of the invention may include one or more known methods, instruments, devices, and compositions, without suffering from the disadvantages and deleterious results.

SUMMARY OF THE INVENTION

Accordingly, there remains a need in the art for an improved method of bone defect repair. More specifically, there remains a need for an improved method of treating osteolytic lesions associated with orthopedic implants that does not require invasive revision surgery. Therefore, it is a feature of an embodiment of the present invention to provide for a method and kit for bone defect repair that fulfills the need in the art. The method includes: accessing the defect in the bone; preparing the defect for receiving a bone growth promoting substance; and delivering the bone growth promoting substance to the defect. The bone growth promoting substance is flexible and capable of adhering to the region of the defect in the bone and provides for the sustained or immediate release of bone growth promoting formulations.

In an embodiment of the invention, the bone defect repair is accomplished in a minimally invasive manner. An access apparatus is used to access the bone defect; a debriding device is used to prepare the bone defect; and a delivery apparatus is used to deliver the bone growth promoting substance to the bone defect.

In another embodiment, there is provided a bone growth promoting substance that is flexible and capable of adhering to the region of the defect in the bone. The bone growth promoting substance comprises a carrier material coated or infused with at least one bone growth promoting formulation.

In another embodiment, there is provided a kit including an access means, a debriding device, and a delivery apparatus. Optionally, the kit may include a quantity of bone growth promoting substance comprising at least one bone growth promoting formulation appropriately formulated to aid repair of a specific defect.

These and other objects and advantages of the present invention will be apparent from the description provided herein.

DESCRIPTION OF THE PREFERRED EMBODIMENTS

The following description is intended to convey a thorough understanding of the embodiments by providing a number of specific embodiments and details involving repair of bone defects. It is understood, however, that the invention is not limited to these specific embodiments and details, which are exemplary only. It is further understood that one possessing ordinary skill in the art, in light of known systems and methods, would appreciate the use of the invention for its intended purposes and benefits in any number of alternative embodiments.

The terminology used herein is for the purpose of describing particular embodiments only and is not intended to limit the scope of the present invention. As used throughout this disclosure, the singular forms "a," "an," and "the" include plural reference unless the context clearly dictates otherwise. Thus, for example, a reference to "a debriding device" includes a plurality of such devices, as well as a single device, and a reference to "an osteoinductive agent" is a reference to one or more agents and equivalents thereof known to those skilled in the art, and so forth.

Unless defined otherwise, all technical and scientific terms used herein have the same meanings as commonly understood by one of ordinary skill in the art to which this invention belongs. All publications mentioned herein are cited for the purpose of describing and disclosing the various access methods, debriding devices, bone growth promoting substances and formulations, osteoinductive agents, and other components that are reported in the publications and that might be used in connection with the invention. Nothing herein is to be construed as an admission that the invention is not entitled to antedate such disclosures by virtue of prior invention.

Throughout this description, the expression "bone defect" refers to any void, crack, fissure, fracture, osteolytic lesion, diseases, disorders or other defect present in the bone of a patient. It is understood that this defect may be the result of any factor that may cause bone defects. Although osteolytic lesions resulting from the implantations of orthopedic devices and subsequent movement of these devices against bone are, at various times, used as an example of a bone defect, it is understood that nothing herein is to be construed to limit the invention to the treatment of osteolytic lesions or any other specific type of bone defect.

The expression "bone growth promoting substance" denotes any substance that promotes the growth of bone. For example, bone growth promoting substances may be osteoinductive, or osteoconductive. The term "osteoinductive" and the expression "bone growth promoting substance" insofar as they refer to agents and formulations, are used interchangeably throughout this description.

As used herein, "bioavailable" shall mean that the bone growth promoting substance, e.g., osteoinductive agents(s) are provided in vivo in the patient, wherein the osteoinductive agent(s) retain biological activity. By retaining biological activity is meant that the osteoinductive agent(s) retain at least 25% activity, more preferably at least 50% activity, still more preferably at least 75% activity, and most preferably at least 95% or more activity of the osteoinductive agent relative to the activity of the osteoinductive agent prior to implantation.

As used herein, "mature polypeptide" shall mean a post-translationally processed form of a polypeptide. For example, mature polypeptides may lack one or more of a signal peptide, prepropeptide and propeptide domains following expression in a host expression system. One of skill in the art of biology is aware of the meanings of signal peptide, prepropeptide and propeptide domains.

As used herein, "immediate release" shall mean formulations of the invention that provide the osteoinductive formulations in a reasonably immediate period of time.

As used herein, "sustained release" shall mean formulations of the invention that are designed to provide osteoinductive formulations at relatively consistent concentrations in bioavailable form over extended periods of time.

As used herein, "biodegradable" shall mean a polymer that degrades during in vivo application. In one embodiment of the invention, the degradation of the polymer produces the polymer monomeric subunits.

Embodiments of the invention include a method and kit for repairing a defect in bone. The method preferably includes accessing the defect in the bone, preparing the defect for receiving a bone growth promoting substance, and delivering the bone growth promoting substance to the defect. The bone growth promoting substance is flexible and capable of adhering to the region of the defect in the bone and provides for the sustained or immediate release of bone growth promoting formulations.

Figure 1:
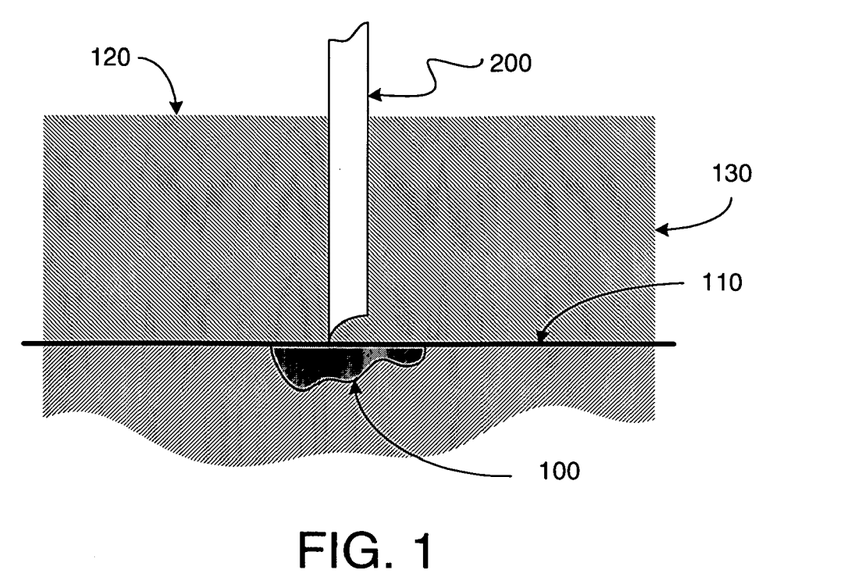
FIG. 1 illustrates a side view of a cross section of a bone having a bone defect, together with the adjacent tissue and a cannula inserted through the tissue to a position adjacent the bone defect.

With reference to FIG. 1, a bone defect 100 is present on the surface of bone 110 below the surface of the skin 120 and soft tissue 130. Although not shown in the figures, but will be appreciated by those skilled in the art, the bone defect 100 can be accessed using conventional open surgical techniques. Suitable techniques include making an incision in the surface of the skin 120, and subsequently cutting or pushing aside tissue (e.g., tendon, muscle, skin, vascular) down to the bone defect 100.

Figure 2:
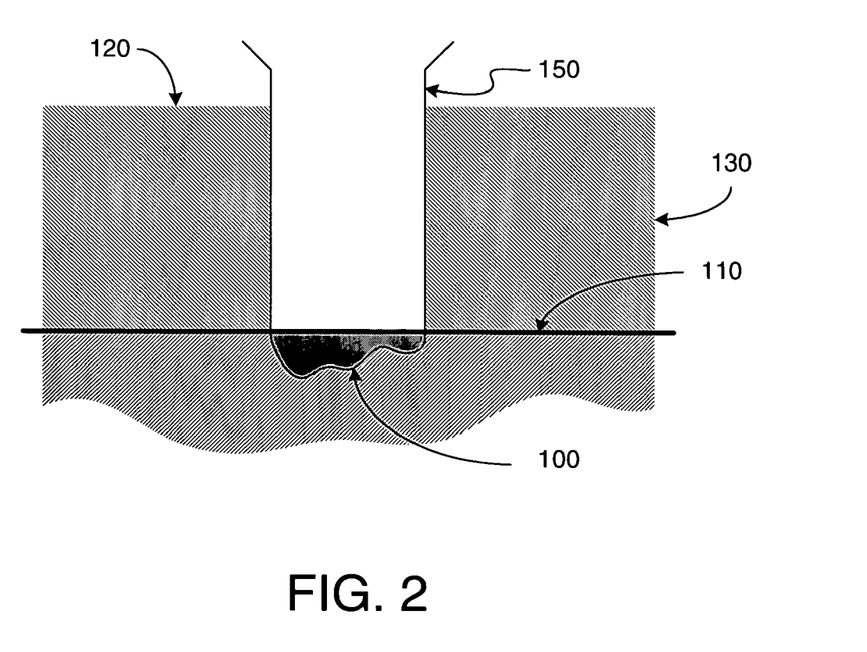
FIG. 2 illustrates the bone and bone defect of FIG. 1 with the access apparatus having dilated the adjacent tissue to provide access to the bone defect.

The bone defect 100 can be accessed by inserting a cannula 200 (or guidewire, not shown) through the skin 120 and soft tissue 130. As illustrated in FIG. 2, the skin 120 and soft tissue 130 can be dilated to provide access to the bone defect 100. In a preferred embodiment, accessing the bone defect can be accomplished in any number of minimally invasive methods known in the art including those illustrated in U.S. Pat. Nos. 5,954,635, 6,206,827, 6,425,859, 4,862,891, 5,158,543, 5,357,983, 6,099,547, 5,762,629, 5,976,146, 6,371,968, 5,163,949, 5,197,971, 5,573,517, 6,187,000, 6,312,443, 4,899,729, 5,139,511, 3,044,461, 3,788,318, 4,716,901, and 6,162,236, and German Patent No. DE 39 36 811, each of which is hereby incorporated by reference.

It is understood that one possessing ordinary skill in the art would appreciate that the method and apparatus described in any of the above listed patents would be suitable for accessing the bone defect. It would also be appreciated by one of ordinary skill in the art that any similar or equivalent method and apparatus would also be suitable for accessing the bone defect. The minimally invasive access methods discussed above constitute the preferred embodiment of the invention. However, the invention is not limited to the methods describe above, nor to minimally invasive methods in general. The invention may make use of any suitable method of accessing the bone defect including traditional, more invasive methods known to one of skill in the art.

Figure 3:
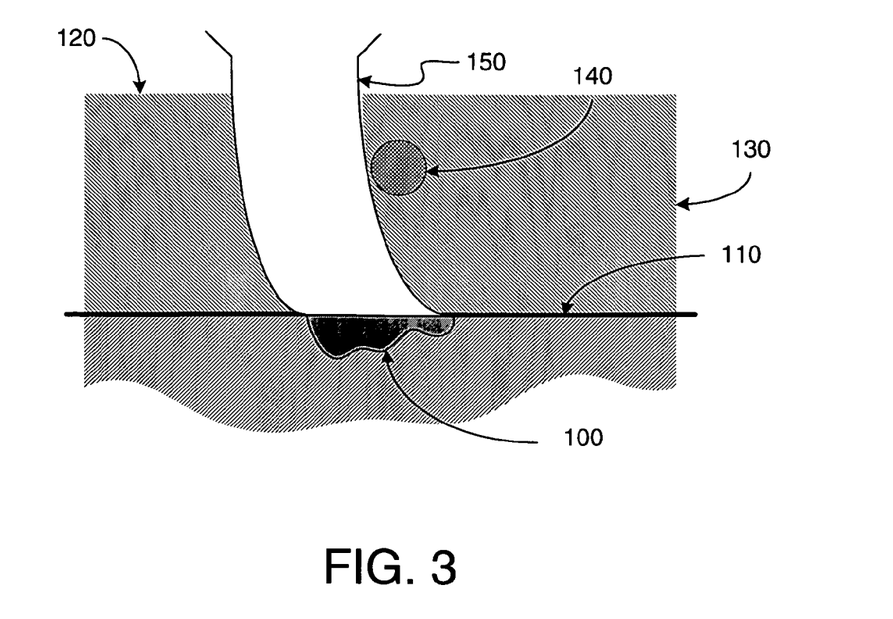
FIG. 3 shows an alternative embodiment of the access apparatus of FIG. 2 wherein the access apparatus is curved to avoid interfering with intervening tissue.
Figure 4:
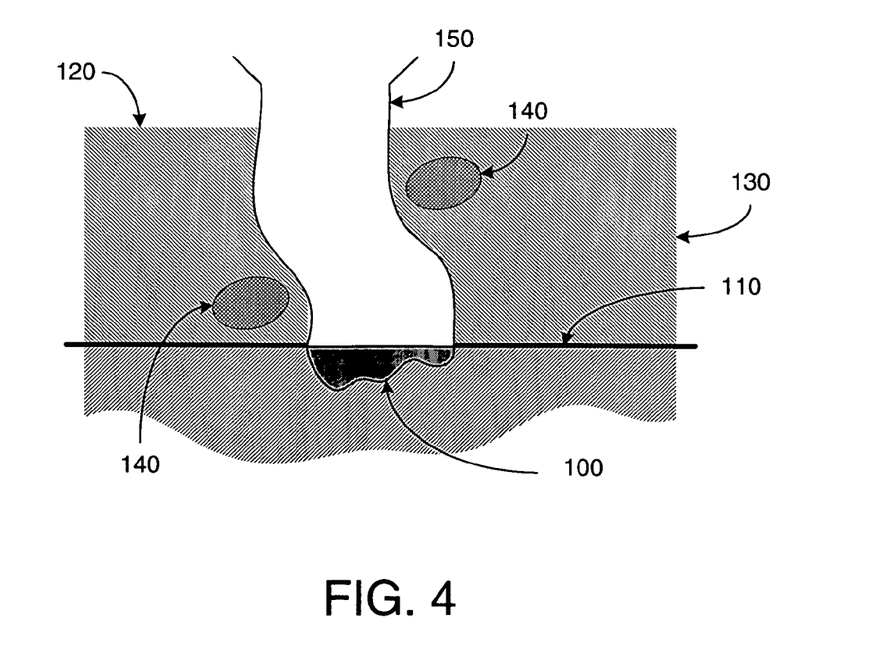
FIG. 4 shows a further embodiment of the access apparatus of FIG. 3.

Additionally, with reference to FIGS. 3 and 4, the access apparatus 150 may be bent, curved or flexible to allow access to the bone defect 100 while avoiding interference with intervening tissue 140 such as major blood vessels, nerves or bone.

Figure 5:
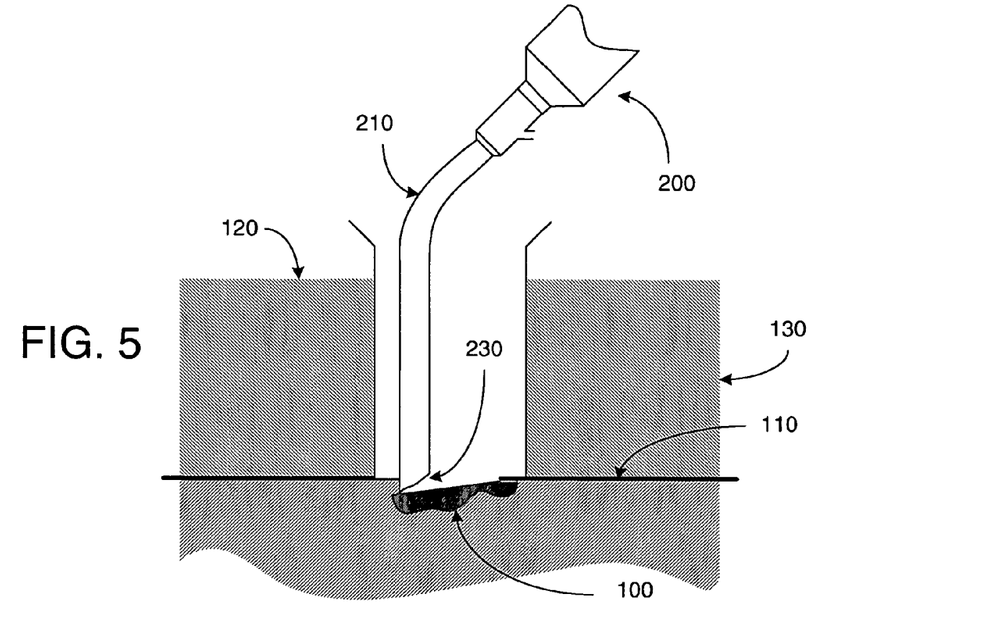
FIG. 5 illustrates the bone defect of FIG. 2 with a rotary cutter inserted through the access apparatus in order to debride the bone defect.
Figure 6:
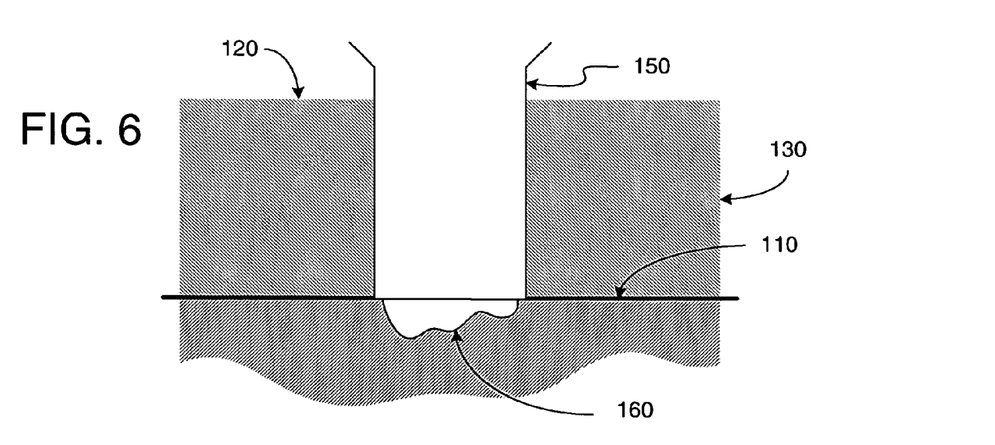
FIG. 6 illustrates the bone defect of FIG. 5 with the bone preparation completed and the bone defect prepared for application of the bone growth promoting substance.
Figure 9:
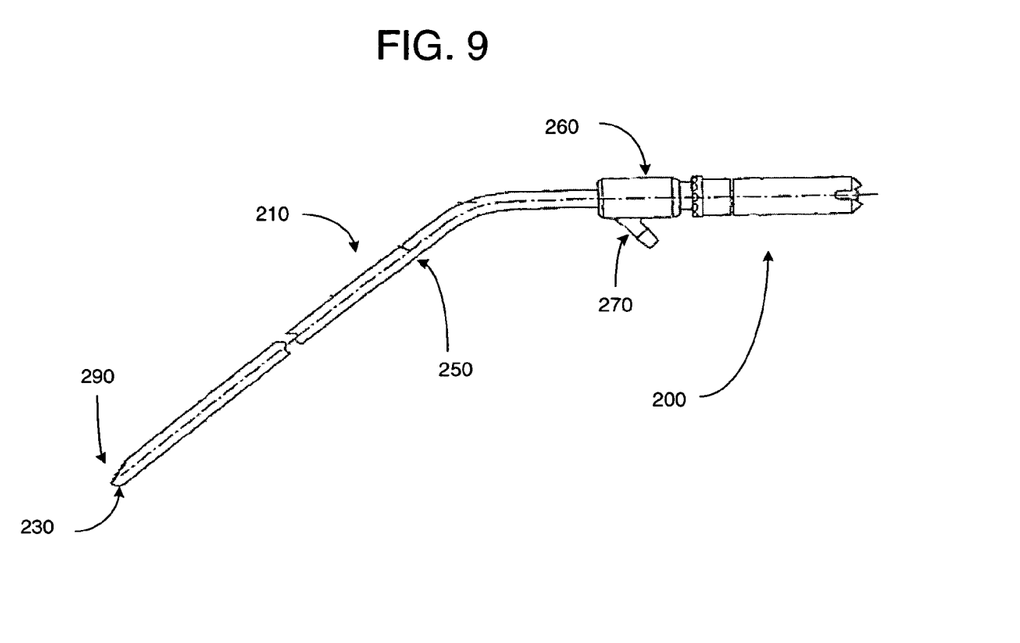
FIG. 9 illustrates one embodiment of a cutting apparatus useful in embodiments of the invention.
Figure 10:
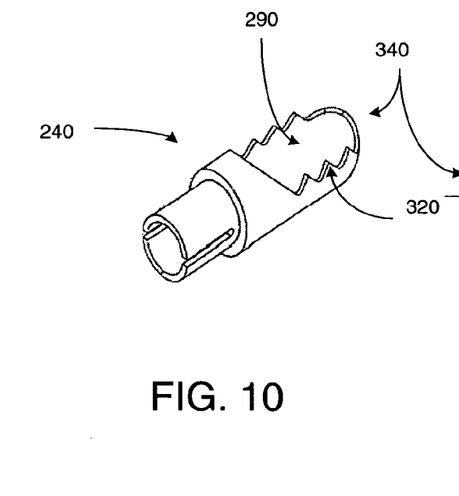
FIG. 10 illustrates an embodiment of the inside portion of a rotary cutter useful in embodiments of the invention.
Figure 11:
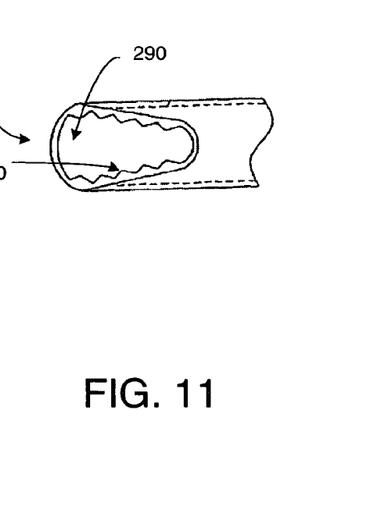
FIG. 11 illustrates an embodiment of a tip of a rotary cutter useful in embodiments of the invention.

Referring to FIG. 5, the bone defect is prepared to receive a bone growth promoting substance. In a preferred embodiment, the bone defect 100 may be prepared by being debrided using a suitable debriding device. In a more preferred embodiment, the debriding device comprises a rotary cutter 200. Appropriate rotary cutters are described in U.S. Pat. Nos. 6,312,441, 6,620,180, 6,238,400, 6,391,016, 6,391,017, 5,685,838, 5,957,881, and 5,922,003, and U.S. Patent Application Publications 2003/0181934 and 2003/0060862, each of which is hereby incorporated by reference. An exemplary rotary cutter, and rotary cutter heads are shown in FIGS. 9, 10, and 11.

The rotary cutter 200 preferably may be configured to facilitate access to the bone defect 100. For example, the cutting blade assembly 210 of the rotary cutter 200 may be bent, angled or curved to allow the cutting blade to more easily access the bone defect. Additionally, the cutting blade assembly may have multiple curves or bends along the length thereof as required by the anatomical situation. Skilled artisans are capable of designing a flexible cutting blade assembly 210, whereby the rotating blade portion is positioned at the distal end 230 of the rotary cutter 200.

Cutting blade assembly 210 for a typical rotary cutter 200 is detachable so that it may be discarded after use. To render the cutting blade assembly 210 flexible, either the detachable blade assembly 210 may be flexible, or an additional flexible connector means (not shown) for connecting the end of the cutter 200 to the end of the cutting blade assembly 210 can be used. Preferably, the cutter 200 includes a suction means for suctioning cut tissue and bone, and an irrigation means. Additional electrical connections can be present in the rotary cutter 200, to provide energy to the tip of the cutting blade assembly 210.

The size, shape, and configuration of the distal end 230 of the cutting blade assembly 210 may be modified to accommodate the location, type and severity of the bone defect in any manner apparent to one of ordinary skill in the art.

One of ordinary skill in the art will appreciate that while the preferred embodiment of the invention makes use of rotary cutters similar or equivalent to those described, the invention is in no way limited to these specific cutters or their equivalents. Indeed, any debriding apparatus can be used to prepare the bone defect. The bone defect may be prepared using any appropriate method including but not limited to suitable scrapers, scalpels, saws, ronguers, and cutters whether powered or manual.

Figure 7:
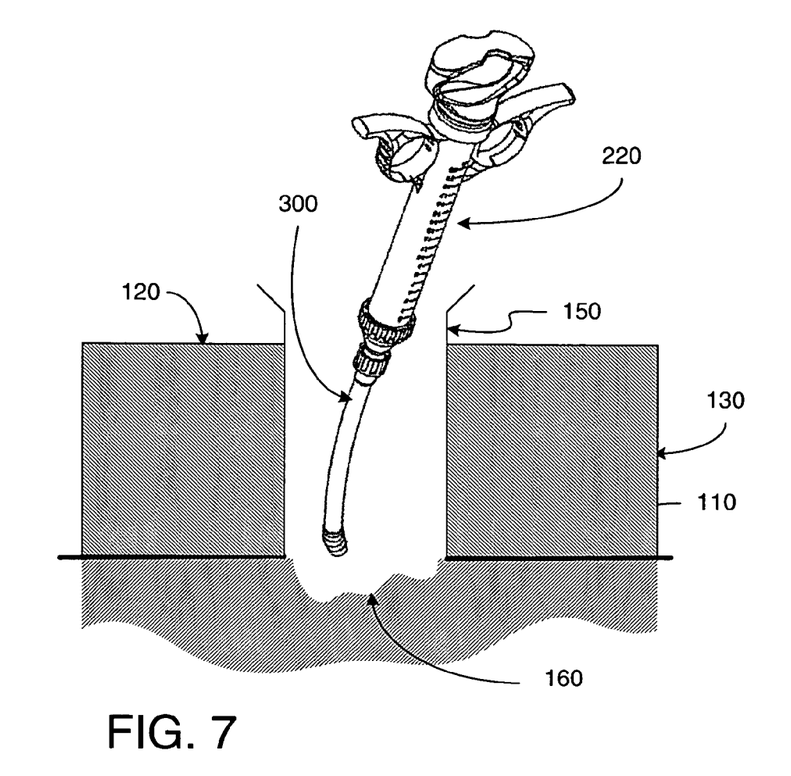
FIG. 7 shows the bone defect of FIG. 6 with a graft syringe inserted though the access apparatus in order to deliver the bone growth promoting substance.
Figure 8:
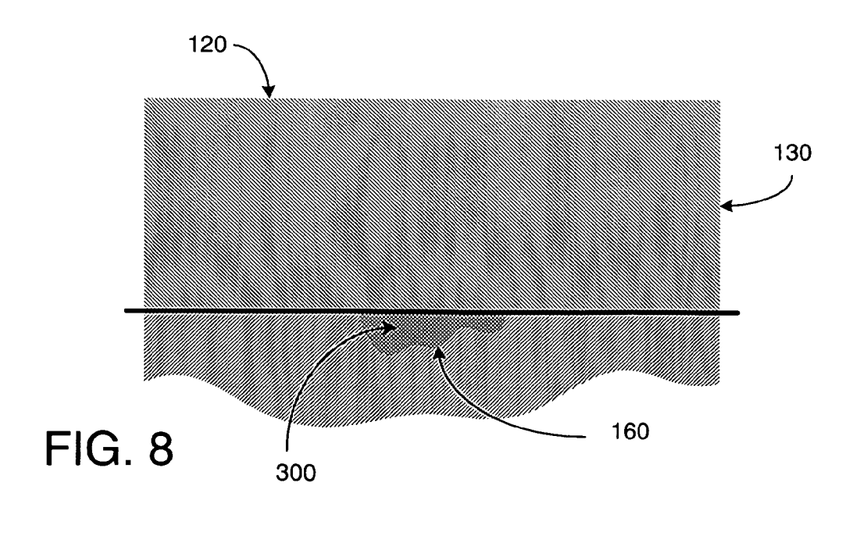
FIG. 8 illustrates the finished procedure with the bone growth promoting substance delivered to the bone defect and the access apparatus removed.

Referring now to FIG. 7, the bone growth promoting substance 300 preferably is delivered to the prepared bone defect 160 using an appropriate delivery method. In a preferred embodiment, the delivery method comprises a graft syringe 220. Alternatively, the delivery apparatus may include a cannula and push rod assembly, as is known in the art. The bone growth promoting substance can be inserted into the cannula, and then pushed into place using the push rod. The bone growth promoting substance 300 is flexible and adheres to the bone 110. Referring to FIG. 8, the delivery 220 and access 150 apparatuses are removed and the growth promoting substance 300 remains adhered to the bone defect location 160.

FIG. 9 illustrates a preferred rotary cutter 200. While FIG. 9 illustrates a bend in the blade assembly 210 closer to a proximal portion than the distal end 230, the bend may be anywhere, or the blade assembly 210, or connecting means (not shown) may be flexible to permit a bend anywhere along the longitudinal axis of the blade assembly 210. The powered rotary cutter 200 is illustrated in FIG. 9 can be driven by any suitable handpiece such as the STRAIGHTSHOT marketed by Xomed Surgical Products, Inc. and shown in U.S. Pat. No. 5,916,231 to Bays, the disclosure of which is incorporated herein by reference.

The blade assembly 210 includes an outer blade member or assembly 250 and a hollow inner blade member assembly 240 (FIG. 10) rotatably received within the outer blade member 250. Outer blade member 250 includes a hub 260 with an irrigation port or coupling 270 extending angularly therefrom. The angled blade assembly 210 extends to a rounded distal end 230 having an opening facing upwardly, away from the center of curvature of the bend, to define a cutting port or window 290. Dependent upon the anatomical situation and requirements, the window 290 can face in any desired direction (i.e. also downwardly or sidewards) and the outer blade member 210 can have multiple curves or bends, along the length thereof.

As best seen in FIGS. 10 and 11, cutting port or window 290 may be beveled (FIG. 11) and includes a plurality of teeth 320 along longitudinal sides thereof with an outer surface or edge 340 of the window being dull or blunt and an inner surface or edge 36 of the window being sharp. Any number of teeth 320 can be used, and the teeth can be configured to cut soft tissue, bone, decayed bone, etc.

The embodiments shown and described with respect to FIG. 7 show the delivery of a bone growth promoting substance to the prepared bone defect 160. The bone growth promoting substance comprises at least one osteoinductive and/or osteoconductive formulation. Appropriate osteoinductive formulations are described in co-pending application Ser. No. 10/931,198, which is hereby incorporated by reference in its entirety. The bone growth promoting substance also may comprise a carrier material containing, coated with or infused with at least one osteoinductive formulation. In one embodiment, the carrier material comprises a biodegradable polymer material. In another embodiment, the carrier material comprises collagen sponge.

In another embodiment, the carrier material comprises granules of any appropriate material, such as demineralized bone granules, calcium phosphate-containing granules, and the like, all of which are well known in the art. In a further embodiment, the carrier material comprises bone putty, which includes any of the known or later discovered bone putties and/or bone cements. It is preferred that the carrier material form a scaffold-like structure to permit the newly grown bone to interpenetrate the matrix, thereby further promoting the strength and growth of the bone. In addition, the bone growth promoting substance may be in the form of any of the aforementioned granules, bone putties, bone cements, in which case the carrier and the osteoinductive and/or osteoconductive formulation are the same material. In another embodiment, the carrier material and osteoinductive and/or osteocunductive formulation optionally are the same material and can comprise allograft, DBM (demineralized bone matrix) calcium phosphates (e.g., hydroxyapatites, and tricalcium phosphates), calcium sulphates, sulphate salts, autograft, and the like, as well as mixtures or combinations of these.

The osteoinductive formulations of the invention preferably comprise one or more osteoinductive agent(s) that induce growth of endogenous bone, or tissues related to the endogenous bone such as connective tissues and vascular tissues. Additionally, osteoinductive agents are provided that function to inhibit bone resorption. The osteoinductive formulations comprise osteoinductive agents, such as for example, one or more Bone Morphogenetic Protein (BMP), one or more Connective Tissue Growth Factor (CTGF), one or more Vascular Endothelial Growth Factor (VEGF), Osteoprotegerin (OPG), Periostin and one or more Transforming Growth Factor-beta (TGF-β) polynucleotides and polypeptides. The osteoinductive agent is provided in bioavailable form from the carrier material as a component of an immediate release or a sustained release formulation.

In one embodiment of the invention, the carrier material comprises biodegradable polymers that release osteoinductive formulation(s) based on the degradation rates of the biodegradeable polymers containing the osteoinductive formulation(s). The invention further provides a method for preventing and treating osteolytic lesion formation in the vicinity of the orthopedic implant in a patient. The invention also provides a method of enhancing the growth of tissues surrounding sites of implantation.

Embodiments of the invention include a bone growth promoting substance comprising osteoinductive formulations useful to promote the growth of endogenous bone, connective tissue and vascular tissue, as well as for the prevention of bone resorption. The osteoinductive formulations useful with the invention include one or more osteoinductive agents. The osteoinductive formulations may be incorporated into the polymer composition that forms the carrier material. Another aspect of the invention relates to osteoinductive formulations incorporated within the carrier material. Osteoinductive formulations preferably include one or more osteoinductive agents, and provide the one or more agents in bioavailable form as either immediate release or sustained release formulations. Osteoinductive formulations further optionally comprise one or more of the following components: antibiotics, carriers, bone marrow aspirate, bone marrow concentrate, demineralized bone matrix, immunosuppressives, agents that enhance isotonicity and chemical stability, and any combination of one or more, including all, of the recited components.

The osteoinductive formulations of embodiments are available as immediate release formulations or sustained release formulations. One of skill in the art of implant surgery is able to determine whether a patient would benefit from immediate release formulations or sustained release formulations based on factors such as age and level of physical activity. Therefore, the osteoinductive formulations of the invention are available as immediate release formulations, sustained release formulations, or both.

Representative immediate release formulations are liquid formulations comprising at least one osteoinductive agent(s) applied to the surface carrier material. The liquid formulations provide osteoinductive agent(s) in bioavailable form at rates dictated by the fluid properties of the liquid formulation, such as diffusion rates at the site of implantation, the influence of endogenous fluids, etc. Examples of suitable liquid formulations comprise water, saline, or other acceptable fluid mediums that will not induce host immune responses. Skilled artisans recognize that the osteoinductive agents need to reside at the situs of defect long enough to promote bone growth, and preferably should not seep to surrounding areas where bone growth is undesired. Using the guidelines provided herein, those skilled in the art are capable of designing a suitable bone growth promoting substance formulation for delivery.

Immediate release formulations of the embodiments provide the osteoinductive formulations in a reasonably immediate period of time, although factors such as proximity to bodily fluids, composition of the formulations, etc, will influence the period of time within which the osteoinductive agent(s) is liberated from the formulations. However, immediate release formulations are not designed to retain the one or more osteoinductive agents for extended periods of time, and typically will lack a biodegradable polymer as a component of the immediate release formulation.

In another embodiment, osteoinductive formulations are available in sustained release formulations that provide the osteoinductive formulation(s) in bioavailable form over extended periods of time. The duration of release from the sustained release formulations is dictated by the nature of the formulation and other factors discussed supra, such as for example proximity to bodily fluids, as well as density of application of the formulations, degradation rates of biodegradeable polymers comprising the osteoinductive formulations, and other factors. However, sustained release formulations are designed to provide osteoinductive agents in the formulations at relatively consistent concentrations in bioavailable form over extended periods of time. Biodegradable sustained release polymers useful with the carrier material are well known in the art and include, but are not limited to, polylactides, polyglycolides, polycaprolactones, polyanhydrides, polyamides, polyurethanes, polyesteramides, polyorthoesters, polydioxanones, polyacetals, polyketals, polycarbonates, polyorthocarbonates, polyphosphazenes, polyhydroxybutyrates, polyhydroxyvalerates, polyalkylene oxalates, polyalkylene succinates, poly(malic acid), poly(amino acids), polyvinylpyrrolidone, polyethylene glycol, polyhydroxycellulose, chitin, chitosan, poly(L-lactic acid), poly(lactide-co-glycolide), poly(hydroxybutyrate-co-valerate), and copolymers, terpolymers, or combinations or mixtures of the above materials. The release profile of the biodegradable polymer can further be modified by inclusion of biostable polymers that influence the biodegradation rate of the polymer composition. Biostable polymers that could be incorporated into the biodegradable polymers, thereby influencing the rates of biodegradation, include but are not limited to silicones, polyesters, vinyl homopolymers and copolymers, acrylate homopolymers and copolymers, polyethers, and cellulosics.

The biodegradable polymers can be solid form polymers or alternatively can be liquid polymers that solidify in a reasonable time after application. Suitable liquid polymers formulations include, but are not limited to those polymer compositions disclosed in, for example, U.S. Pat. Nos. 5,744,153, 4,938,763, 5,278,201 and 5,278,202, the contents of each of which are herein incorporated by reference in their entireties. These patents disclose liquid polymer compositions that are useful as controlled drug-release compositions or as implants. The liquid prepolymer has at least one polymerizable ethylenically unsaturated group (e.g., an acrylic-ester-terminated prepolymer). If a curing agent is employed, the curing agent is typically added to the composition just prior to use. The osteoinductive agents are added to the liquid prepolymer prior to curing or fixing of the prepolymer. The prepolymer remains a liquid for a short period of time after the introduction of the curing agent. The mixture then solidifies to form a solid composition. The liquid polymer compositions may be administered to a patient in liquid form, and will then solidify or cure at the site of introduction to form a solid polymer coating composition. Biodegradable forms of the polymers are contemplated, and mixtures of biodegradable and biostable polymers that influence the rate of biodegradation of the polymer are further contemplated.

Osteoinductive formulations of the embodiments further contemplate the use of aqueous and non-aqueous peptide formulations that maintain stability of the osteoinductive agents over extended periods of time. Non-limiting examples of aqueous and non-aqueous formulations useful for the long-term stability of osteoinductive agent(s) include those formulations provided in U.S. Pat. Nos. 5,916,582; 5,932,547, and 5,981,489, the disclosures of each of which are herein incorporated by reference.

A sustained release formulation can be prepared by dispensing an amount of the liquid sustained-release polymer composition onto the carrier material, by, for example, spraying, painting or squirting, whereby the liquid formulation solidifies following administration to provide the sustained release formulation.

In another embodiment, the liquid compositions that are useful for the delivery of osteoinductive formulations in vivo include conjugates of the osteoinductive agent with a water-insoluble biocompatible polymer, with the dissolution of the resultant polymer-active agent conjugate in a biocompatible solvent to form a liquid polymer system. In addition, the liquid polymer system may also include a water-insoluble biocompatible polymer that is not conjugated to the osteoinductive agent. In one embodiment, these liquid compositions may be introduced into the body of a subject in liquid form. The liquid composition then solidifies or coagulates in situ to form a controlled release implant where the osteoinductive agent is conjugated to the solid matrix polymer.

Osteoinductive agents of embodiments can be administered in the osteoinductive formulations as isolated polypeptides or polynucleotides. Polynucleotide compositions of the isolated osteoinductive agents include, but are not limited to, isolated Bone Morphogenetic Protein (BMP), Vascular Endothelial Growth Factor (VEGF), Connective Tissue Growth Factor (CTGF), Osteoprotegerin, Periostin and Transforming Growth Factor beta (TGF-β) polynucleotides. Polynucleotide compositions of the osteoinductive agents include, but are not limited to, gene therapy vectors harboring polynucleotides encoding the osteoinductive polypeptides of interest. Gene therapy methods require a polynucleotide that codes for the osteoinductive polypeptide operatively linked or associated to a promoter and any other genetic elements necessary for the expression of the osteoinductive polypeptide by the target tissue. Such gene therapy and delivery techniques are known in the art. See, for example, International Publication No. WO90/11092, the disclosure of which is incorporated herein by reference in its entirety. Suitable gene therapy vectors include, but are not limited to, gene therapy vectors that do not integrate into the host genome. Alternatively, suitable gene therapy vectors include, but are not limited to, gene therapy vectors that integrate into the host genome.

In one embodiment, the polynucleotide of the invention is delivered in plasmid formulations. Plasmid DNA or RNA formulations refer to sequences encoding osteoinductive polypeptides that are free from any delivery vehicle that acts to assist, promote or facilitate entry into the cell, including viral sequences, viral particles, liposome formulations, lipofectin or precipitating agents and the like. Optionally, gene therapy compositions of the embodiments can be delivered in liposome formulations and lipofectin formulations, which can be prepared by methods well known to those skilled in the art. General methods are described, for example, in U.S. Pat. Nos. 5,593,972, 5,589,466, and 5,580,859, which are herein incorporated by reference.

Gene therapy vectors further comprise suitable adenoviral vectors including, but not limited to for example, those described in Kozarsky and Wilson, Curr. Opin. Genet. Devel., 3:499-503 (1993); Rosenfeld et al., Cell, 68:143-155 (1992); Engelhardt et al., Human Genet. Ther., 4:759-769 (1993); Yang et al., Nature Genet., 7:362-369 (1994); Wilson et al., Nature, 365:691-692 (1993); and U.S. Pat. No. 5,652,224, which are herein incorporated by reference.

Polypeptide compositions of the isolated osteoinductive agents include, but are not limited to, isolated Bone Morphogenetic Protein (BMP), Vascular Endothelial Growth Factor (VEGF), Connective Tissue Growth Factor (CTGF), Osteoprotegerin, Periostin and Transforming Growth Factor beta (TGF-β) polypeptides. Polypeptide compositions of the osteoinductive agents include, but are not limited to, isolated full-length proteins, fragments and variants thereof. In a preferred embodiment, polypeptide fragments of the osteoinductive agents comprise, or alternatively consist of, propeptide forms of the isolated full-length polypeptides. In a particularly preferred embodiment, polypeptide fragments of the osteoinductive agents comprise, or alternatively consist of, mature forms of the isolated full-length polypeptides. Also preferred are the polynucleotides encoding the propeptide and mature polypeptides of the osteoinductive agents.

Variants of the osteoinductive agents of the embodiments include, but are not limited to, protein variants that are designed to increase the duration of activity of the osteoinductive agent in vivo. Preferred embodiments of variant osteoinductive agents include, but are not limited to, full length proteins or fragments thereof that are conjugated to polyethylene glycol (PEG) moieties to increase their half-life in vivo (also known as pegylation). Methods of pegylating polypeptides are well known in the art (See, e.g., U.S. Pat. No. 6,552,170 and European Patent No. 0,401,384 as examples of methods of generating pegylated polypeptides).

In another embodiment, the osteoinductive agent(s) are provided in the osteoinductive formulation(s) as fusion proteins. In one embodiment, the osteoinductive agent(s) are available as fusion proteins with the $F_C$ portion of human IgG. In another embodiment, the osteoinductive agent(s) of the invention are available as hetero- or homodimers or multimers. Examples of preferred fusion proteins include, but are not limited to, ligand fusions between mature osteoinductive polypeptides and the $F_C$ portion of human Immunoglobulin G (IgG). Methods of making fusion proteins and constructs encoding the same are well known in the art.

Osteoinductive agents of the embodiments that are included with the osteoinductive formulations preferably are sterile. In a non-limiting method, sterility is readily accomplished for example by filtration through sterile filtration membranes (e.g., 0.2 micron membranes or filters).

In one embodiment of the invention, the carrier material is provided without osteoinductive formulations incorporated within the carrier material. In this embodiment of the invention, the osteoinductive formulations are introduced into the carrier material prior to implantation of the material in a patient. In such a situation, osteoinductive agents generally are placed into a container having a sterile access port, for example, an intravenous solution bag or vial having a stopper pierceable by a hypodermic injection needle. In one embodiment, osteoinductive agents and prepared osteoinductive formulations are stored in separate containers, for example, sealed ampoules or vials, as an aqueous solution or as a lyophilized formulation for reconstitution. As an example of a lyophilized formulation, 10-ml vials are filled with 5 ml of sterile-filtered 1% (w/v) aqueous osteoinductive agent solution, and the resulting mixture is lyophilized. The osteoinductive agent is prepared by reconstituting the lyophilized agent prior to administration in an appropriate solution, admixed with the prepared osteoinductive formulations and administered to the surface of the carrier material or infused into the carrier material prior to or concurrent with implantation into a patient. Application may be achieved by immersion of the carrier material in osteoinductive formulations, by spraying osteoinductive formulations on the surface of the carrier material, or by any other means of application.

As one of skill in the art will recognize, the concentrations of osteoinductive agent can be variable based on the desired length or degree of osteoinduction. Similarly, one of skill in the art will understand that the duration of sustained release can be modified by the manipulation of the compositions comprising the sustained release formulation, such as for example, modifying the percent of biostable polymers found within a sustained release polymer.

A method to provide liquid compositions that are useful to form polymeric material for the delivery of osteoinductive agents in vivo is to conjugate the active agent with a water-insoluble biocompatible polymer and dissolve the resultant polymer-active agent conjugate in a biocompatible solvent to form a liquid polymer system similar to that described in U.S. Pat. Nos. 4,938,763, 5,278,201 and 5,278,202. The water-insoluble biocompatible polymers may be those described in the above patents or related copolymers. In addition, the liquid polymer system may also include a water-insoluble biocompatible polymer that is not conjugated to the active agent. In one embodiment of the invention, these liquid compositions may be introduced into the body of a subject in liquid form. The liquid composition then solidifies or coagulates in situ to form a controlled release implant where the active agent is conjugated to the solid matrix polymer.

Osteoinductive formulations of the embodiments optionally further comprise de-mineralized bone matrix compositions (hereinafter "DBM" compositions), bone marrow aspirate, bone marrow concentrate, or combinations or permutations of any of the same. Methods for producing DBM are well known in the art, and DBM may be obtained following the teachings of O'Leary et al (U.S. Pat. No. 5,073,373) or by obtaining commercially available DBM formulations such as, for example, AlloGro® available from suppliers such as AlloSource® (Centennial, Colo.). Methods of obtaining bone marrow aspirates as well as devices facilitating extraction of bone marrow aspirate are well known in the art and are described, for example, by Turkel et al in U.S. Pat. No. 5,257,632.

Osteoinductive formulations of the embodiments optionally further comprise antibiotics that may be administered with the osteoinductive agent. As discussed by Vehmeyer et al., the possibility exists that bacterial contamination can occur for example due to the introduction of contaminated allograft tissue from living donors. Vehmeyer, S B, et al., *Acta Orthop Scand.*, 73(2): 165-169 (2002). Antibiotics of the invention are also co-administered with the osteoinductive formulations to prevent infection by obligate or opportunistic pathogens that are introduced to the patient during surgery.

Antibiotics useful with the osteoinductive formulations of the embodiments include, but are not limited to, amoxicillin, beta-lactamases, aminoglycosides, beta-lactam (glycopeptide), clindamycin, chloramphenicol, cephalosporins, ciprofloxacin, erythromycin, fluoroquinolones, macrolides, metronidazole, penicillins, quinolones, rapamycin, rifampin, streptomycin, sulfonamide, tetracyclines, trimethoprim, trimethoprim-sulfamthoxazole, and vancomycin. In addition, one skilled in the art of implant surgery or administrators of locations in which implant surgery occurs may prefer the introduction of one or more of the above-recited antibiotics to account for nosocomial infections or other factors specific to the location where the surgery is conducted. Accordingly, the embodiments further contemplate that one or more of the antibiotics described herein, and any combination of one or more of the same antibiotics, may be included in the osteoinductive formulations.

The osteoinductive formulations of the embodiments optionally further comprise immunosuppressive agents, particularly in circumstances where allograft compositions are administered to the patient. Suitable immunosuppressive agents that may be administered in combination with the osteoinductive formulations of the invention include, but are not limited to, steroids, cyclosporine, cyclosporine analogs, cyclophosphamide, methylprednisone, prednisone, azathioprine, FK-506, 15-deoxyspergualin, and other immunosuppressive agents that act by suppressing the function of responding T cells. Other immunosuppressive agents that may be administered in combination with the osteoinductive formulations include, but are not limited to, prednisolone, methotrexate, thalidomide, methoxsalen, rapamycin, leflunomide, mizoribine (bredinin™), brequinar, deoxyspergualin, and azaspirane (SKF 105685), Orthoclone OKT™ 3 (muromonab-CD3). Sandimmune™, Neoral™, Sangdya™ (cyclosporine), Prograf™ (FK506, tacrolimus), Cellcept™ (mycophenolate motefil, of which the active metabolite is mycophenolic acid), Imuran™ (azathioprine), glucocorticosteroids, adrenocortical steroids such as Deltasone™ (prednisone) and Hydeltrasol™ (prednisolone), Folex™ and Mexate™ (methotrxate), Oxsoralen-Ultra™ (methoxsalen) and Rapamuen™ (sirolimus).

Osteoinductive formulations may optionally further comprise a carrier vehicle such as water, saline, Ringer's solution, calcium phosphate based carriers, or dextrose solution. Non-aqueous vehicles such as fixed oils and ethyl oleate are also useful herein, as well as liposomes.

In one embodiment, collagen is used as a carrier material for the delivery of osteoinductive formulations. In another embodiment, collagen in combination with glycosaminoglycan is utilized as a carrier material for the osteoinductive formulations, as described in U.S. Pat. No. 5,922,356, which is herein incorporated by reference. The content of glycosaminoglycan in the formulation is preferably less than 40% by weight of the formulation, more preferably 1-10%. Collagen is preferably 20-95% by weight of the formulation, more preferably 40-60 (wt/wt) %.

Any collagen may be used as a carrier for osteoinductive formulations. Examples of suitable collagen to be used as a carrier include, but are not limited to, human collagen type I, human collagen type II, human collagen type III, human collagen type IV, human collagen type V, human collagen type VI, human collagen type VII, human collagen type VIII, human collagen type IX, human collagen type X, human collagen type XI, human collagen type XII, human collagen type XIII, human collagen type XIV, human collagen type XV, human collagen type XVI, human collagen type XVII, human collagen type XVIII, human collagen type XIX, human collagen type XXI, human collagen type XXII, human collagen type XXIII, human collagen type XXIV, human collagen type XXV, human collagen type XXVI, human collagen type XXVII, and human collagen type XXVIII, and combinations thereof. Collagen carriers useful with the embodiments further comprise, or alternatively consist of, hetero- and homo-trimers of any of the above-recited collagen types. In a preferred embodiment, collagen carriers comprise, or alternatively consist of, hetero- or homo-trimers of human collagen type I, human collagen type II, and human collagen type III, or combinations thereof.

The collagen utilized as a carrier material may be human or non-human, as well as recombinant or non-recombinant. In a preferred embodiment, the collagen utilized as a carrier is recombinant collagen. Methods of making recombinant collagen are known in the art, for example, by using recombinant methods such as those methods described in U.S. Pat. No. 5,895,833 (trangenic production), J. Myllyharju, et al., Biotechnology of Extracellular Matrix, 353-357 (2000) (production of recombinant human types I-III in *Pichia pastoris*), Wong Po Foo, C., et al., Adv. Drug Del. Rev., 54:1131-1143 (2002), or by Toman, P. D., et al., J. Biol. Chem., 275(30): 23303-23309 (2001), the disclosures of each of which are herein incorporated by reference. Alternatively, recombinant human collagen types are obtained from commercially available sources, such as for example, as provided by FibroGen (San Francisco, Calif.).

Some osteoinductive formulations further optionally include substances that enhance isotonicity and chemical stability. Such materials are non-toxic to patients at the dosages and concentrations employed, and include buffers such as phosphate, citrate, succinate, acetic acid, and other organic acids or their salts; antioxidants such as ascorbic acid; low molecular weight (less than about ten residues) polypeptides, e.g., polyarginine or tripeptides; proteins, such as serum albumin, gelatin, or immunoglobulins; amino acids, such as glycine, glutamic acid, aspartic acid, or arginine; monosaccharides, disaccharides, and other carbohydrates including cellulose or its derivatives, glucose, mannose, or dextrins; chelating agents such as EDTA; sugaralcohols such as mannitol or sorbitol; counterions such as sodium; and/or nonionicsurfactants such as polysorbates, poloxamers, or PEG.

Osteoinductive formulations of the embodiments further comprise isolated osteoinductive agents. Isolated osteoinductive agents promote the growth of endogenous bone, or aid in preventing resorption of bone tissue surrounding the implant by osteoclasts. Isolated osteoinductive agents are available as polypeptides or polynucleotides. Isolated osteoinductive agents comprise full-length proteins and fragments thereof, as well as polypeptide variants or mutants of the isolated osteoinductive agents provided herein.

In another embodiment, osteoinductive agent polypeptides are available as heterodimers or homodimers, as well as multimers or combinations thereof.

Recombinantly expressed proteins may be in native forms, truncated analogs, muteins, fusion proteins, and other constructed forms capable of inducing bone, cartilage, or other types of tissue formation as demonstrated by in vitro and ex vivo bioassays and in vivo implantation in mammals, including humans.

Embodiments of the invention further contemplate the use of polynucleotides and polypeptides having at least 95% homology, more preferably 97%, and even more preferably 99% homology to the isolated osteoinductive agent polynucleotides and polypeptides provided herein. Typical osteoinductive formulations comprise isolated osteoinductive agent at concentrations of from about 0.1 mg/ml to 100 mg/ml, preferably 1-10 mg/ml, at a pH of about 3 to 8.

In one embodiment, isolated osteoinductive agents include one or more polynucleotides or polypeptides of members of the family of Bone Morphogenetic Proteins ("BMPs"). BMPs are a class of proteins thought to have osteoinductive or growth-promoting activities on endogenous bone tissue. Known members of the BMP family include, but are not limited to, BMP-1, BMP-2, BMP-3, BMP-4, BMP-5, BMP-6, BMP-7, BMP-8, BMP-9, BMP-10, BMP-11, BMP-12, BMP-13, BMP-15, BMP-16, BMP-17, and BMP-18.

BMPs useful as isolated osteoinductive agents are described in co-pending application Ser. No. 10/931,198, which is hereby incorporated by reference in its entirety.

BMPs utilized as osteoinductive agents, or alternatively consist of, one or more of BMP-1; BMP-2; BMP-3; BMP-4; BMP-5; BMP-6; BMP-7; BMP-8; BMP-9; BMP-10; BMP-11; BMP-12; BMP-13; BMP-15; BMP-16; BMP-17; and BMP-18; as well as any combination of one or more of these BMPs, including full length BMPs or fragments thereof, or combinations thereof, either as polypeptides or polynucleotides encoding said polypeptide fragments of all of the recited BMPs. The isolated BMP osteoinductive agents may be administered as polynucleotides, polypeptides, or combinations of both.

In a particularly preferred embodiment, isolated osteoinductive agents comprise, or alternatively consist of, BMP-2 polynucleotides or polypeptides or mature fragments of the same.

In another embodiment, isolated osteoinductive agents include osteoclastogenesis inhibitors to inhibit bone resorption of the bone tissue surrounding the site of implantation of the implant by osteoclasts.

Osteoclast and Osteoclastogenesis inhibitors include, but are not limited to, Osteoprotegerin polynucleotides and polypeptides corresponding to those described in co-pending application Ser. No. 10/931,198, as well as mature Osteoprotegerin polypeptides and polynucleotides encoding the same. Osteoprotegerin is a member of the TNF-receptor superfamily and is an osteoblast-secreted decoy receptor that functions as a negative regulator of bone resorption. This protein specifically binds to its ligand, osteoprotegerin ligand (TNFSF11/OPGL), both of which are key extracellular regulators of osteoclast development.

Osteoclastogenesis inhibitors further include, but are not limited to, chemical compounds such as bisphosphonate, 5-lipoxygenase inhibitors such as those described in U.S. Pat. Nos. 5,534,524 and 6,455,541 (the contents of which are herein incorporated by reference), heterocyclic compounds such as those described in U.S. Pat. No. 5,658,935 (herein incorporated by reference), 2,4-dioxoimidazolidine and imidazolidine derivative compounds such as those described in U.S. Pat. Nos. 5,397,796 and 5,554,594 (the contents of which are herein incorporated by reference), sulfonamide derivatives such as those described in U.S. Pat. No. 6,313,119 (herein incorporated by reference), and acylguanidine compounds such as those described in U.S. Pat. No. 6,492,356 (herein incorporated by reference).

In another embodiment, isolated osteoinductive agents include one or more polynucleotides or polypeptides of members of the family of Connective Tissue Growth Factors ("CTGFs"). CTGFs are a class of proteins thought to have growth-promoting activities on connective tissues. Known members of the CTGF family include, but are not limited to, CTGF-1, CTGF-2, and CTGF-4. CTGFs useful as isolated osteoinductive agents include, but are not limited to, the CTGFs described in co-pending application Ser. No. 10/931,198.

In another embodiment, isolated osteoinductive agents include one or more polynucleotides or polypeptides of members of the family of Vascular Endothelial Growth Factors ("VEGFs"). VEGFs are a class of proteins thought to have growth-promoting activities on vascular tissues. Known members of the VEGF family include, but are not limited to, VEGF-A, VEGF-B, VEGF-C, VEGF-D and VEGF-E. VEGFs useful as isolated osteoinductive agents include, but are not limited to, the VEGFs described in co-pending application Ser. No. 10/931,198.

In another embodiment, isolated osteoinductive agents include one or more polynucleotides or polypeptides of Transforming Growth Factor-beta genes ("TGF-βs"). TGF-βs are a class of proteins thought to have growth-promoting activities on a range of tissues, including connective tissues. Known members of the TGF-β family include, but are not limited to, TGF-β-1, TGF-β-2, and TGF-β-3. TGF-βs useful as isolated osteoinductive agents include, but are not limited to, the TGF-βs described in co-pending application Ser. No. 10/931,198.

In another embodiment, isolated osteoinductive agents include polynucleotides and polypeptides promoting bone adhesion, such as Periostin polynucleotides and polypeptides that are thought to function as adhesion molecules in bone formation. Bone adhesion promoters include, but are not limited to, Periostin polynucleotides and polypeptides described in co-pending application Ser. No. 10/931,198.

In another embodiment, isolated osteoinductive agents include one or more members of any one of Bone Morphogenetic Proteins (BMPs), Connective Tissue Growth Factors (CTGFs), Vascular Endothelial Growth Factors (VEGFs), Osteoprotegerin or any of the other osteoclastogenesis inhibitors, Periostin, and Transforming Growth Factor-betas (TGF-βs), and any combination of these osteoinductive agents.

The present invention also relates to vectors containing the osteoinductive polynucleotides of the present invention, host cells, and the production of osteoinductive polypeptides by recombinant techniques. The vector may be, for example, a phage, plasmid, viral, or retroviral vector. Retroviral vectors may be replication competent or replication defective. In the latter case, viral propagation generally will occur only in complementing host cells.

The polynucleotides may be joined to a vector containing a selectable marker for propagation in a host. Generally, a plasmid vector is introduced in a precipitate, such as a calcium phosphate precipitate, or in a complex with a charged lipid. If the vector is a virus, it may be packaged in vitro using an appropriate packaging cell line and then transduced into host cells. Useful vectors include, but are not limited to, plasmids, bacteriophage, insect and animal cell vectors, retroviruses, cosmids, and other single and double-stranded viruses.

The polynucleotide insert should be operatively linked to an appropriate promoter, such as the phage lambda PL promoter, the *E. coli* lac, trp, phoA and tac promoters, the SV40 early and late promoters and promoters of retroviral LTRs, to name a few. The skilled artisan will know other suitable promoters. The expression constructs will further contain sites for transcription initiation, termination; origin of replication sequence, and, in the transcribed region, a ribosome binding site for translation. The coding portion of the transcripts expressed by the constructs will preferably include a translation initiating codon at the beginning and a termination codon (UAA, UGA or UAG) appropriately positioned at the end of the polypeptide to be translated.

The expression construct may further contain sequences such as enhancer sequences, efficient RNA processing signals such as splicing and polyadenylation signals, sequences that enhance translation efficiency, and sequences that enhance protein secretion.

Expression systems and methods of producing osteoinductive agents, such as recombinant proteins or protein fragments, are well known in the art. For example, methods of producing recombinant proteins or fragments thereof using bacterial, insect or mammalian expression systems are well known in the art. (See, e.g., Molecular Biotechnology: Principles and Applications of Recombinant DNA, B. R. Glick and J. Pasternak, and M. M. Bendig, Genetic Engineering, 7, pp. 91-127 (1988), for a discussion of recombinant protein production).

The expression vectors will preferably include at least one selectable marker. Such markers include dihydrofolate reductase, G418 or neomycin resistance for eukaryotic cell culture and tetracycline, kanamycin or ampicillin resistance genes for culturing in *E. coli* and other bacteria. Representative examples of appropriate host cells for expression include, but are not limited to, bacterial cells, such as *E. coli, Streptomyces* and *Salmonella typhimurium* cells; fungal cells, such as *Pichia, Saccharomyces* and other yeast cells; insect cells such as *Drosophila* S2 and *Spodoptera* Sf9 and Sf21 cells; animal cells such as CHO, COS, 293, and Bowes melanoma cells; and plant cells. Appropriate culture mediums and conditions for the above-described host cells are known in the art.

Examples of vectors for use in prokaryotes include pQE30Xa and other pQE vectors available as components in pQE expression systems available from QIAGEN, Inc. (Valencia, Calif.); pBluescript vectors, Phagescript vectors, pNH8A, pNH16a, pNH18A, pNH46A, available from Stratagene Cloning Systems, Inc. (La Jolla, Calif.); and Champion™, T7, and pBAD vectors available from Invitrogen (Carlsbad, Calif.). Other suitable vectors will be readily apparent to the skilled artisan.

Introduction of the construct into the host cell can be effected by calcium phosphate transfection, DEAE-dextran mediated transfection, cationic lipid-mediated transfection, electroporation, transduction, infection, or other methods. Such methods are described in many standard laboratory manuals, such as Davis et al., Basic Methods In Molecular Biology (1986).

A polypeptide can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification.

In another embodiment, osteoinductive agents can be produced using bacterial lysates in cell-free expression systems that are well known in the art. Commercially available examples of cell-free protein synthesis systems include the EasyXpress System from Qiagen, Inc. (Valencia, Calif.).

Polypeptides can also be recovered from the following: products of chemical synthetic procedures; and products produced by recombinant techniques from a prokaryotic or eukaryotic host, including, for example, bacterial, yeast, higher plant, insect, and mammalian cells.

Depending upon the host employed in a recombinant production procedure, the polypeptides may be glycosylated or may be non-glycosylated. In addition, polypeptides also may include an initial modified methionine residue, in some cases as a result of host-mediated processes. Thus, it is well known in the art that the N-terminal methionine encoded by the translation initiation codon generally is removed with high efficiency from any protein after translation in all eukaryotic cells. While the N-terminal methionine on most proteins also is efficiently removed in most prokaryotes, for some proteins, this prokaryotic removal process is inefficient, depending on the nature of the amino acid to which the N-terminal methionine is covalently linked.

The osteoinductive agents of the embodiments also may be isolated from natural sources of polypeptide. Osteoinductive agents may be purified from tissue sources, preferably mammalian tissue sources, using conventional physical, immunological and chemical separation techniques known to those of skill in the art. Appropriate tissue sources for the desired osteoinductive agents are known or are available to those of skill in the art.

The bone growth promoting substances of the invention are useful for the treatment of a number of bone defect disorders, as well as other disorders associated with orthopedic implant devices. For example, the bone growth promoting substances are useful for preventing and/or treating the deleterious effects of osteolysis in bone tissues surrounding the site of implantation of an orthopedic device. In a non-limiting hypothesis, the bone growth promoting substance is useful in preventing and/or treating osteolysis through osteoinductive activity attributable to the osteoinductive agents contained within the carrier material.

In another embodiment, the bone growth promoting substance also is useful in promoting vascularization of tissues surrounding a site of implantation that may be damaged or destroyed as a result of implant surgery, or alternatively as a result of a prior or subsequent trauma, disease or injury necessitating the implantation. Similarly, the bone growth promoting substance is useful in promoting the growth of connective tissues surrounding the site of implantation. This is also useful for promoting the regrowth of connective tissues that were damaged or destroyed as a result of implantation surgery or as a result of a prior trauma, disease or injury necessitating the implantation.

Bone growth promoting substances are useful in revision surgeries, such as shoulder surgeries at the stem of the humeral component; in elbow surgeries, at the stem of the humeral and ulna components; in wrist surgeries, at the stem of the ulna component; in hip surgeries, at the femoral stem, associated with acetabular cup implants, and associated with bone screws; and in knee surgeries, at the femoral stem, at the back side of femoral component articulation, at the tibia stem, and the underside of the tibia tray, and at the backside of the patella.

In another embodiment, bone growth promoting substances of the invention are useful for the treatment of diseases and disorders that include, but are not limited to, osteogenesis imperfecta; Hurler syndrome; Marfan syndrome; negative effects associated with hypophosphatasia; infectious, non-infectious, rheumatiod and psoriatic arthritis; relapsing polychondritis; homocystinuria; Ehlers-Danlos syndrome; pseudoxanthoma elasticum; and cutis laxa.

In an additional aspect of the invention, the access apparatus, debriding device (preferably a rotary cutter), and delivery apparatus, or optionally, just the debriding device and delivery apparatus, are packaged in kits under sterile conditions. In one embodiment, a bone growth promoting substance is not packaged with the kit but is instead packaged separately. It is believed that a medical practitioner skilled in the art of orthopedic medicine is best able to ascertain and judge the nature, degree and duration of osteoinductive activity desired in any given patient. By packaging a bone growth promoting substance separately from the kit, the medical practitioner may select the most appropriate carrier materials and osteoinductive formulations for the patients' particular situation.

In a further embodiment, the access apparatus, debriding device, delivery apparatus and at least one growth promoting substance are packaged in kits under sterile conditions based on the nature of the desired osteoinductive formulations. The kits of the invention further optionally comprise instructions for the preparation and administration of the bone defect repair method.

The invention may be practiced in ways other than those particularly described in the foregoing description and examples. Numerous modifications and variations of the invention are possible in light of the above teachings and, therefore, are within the scope of the appended claims.

The entire disclosure of each document cited (including patents, patent applications, journal articles, abstracts, manuals, books, or other disclosures) in the disclosure is herein incorporated by reference in their entireties.

The invention has been described with specific reference to particularly preferred embodiments and examples. Those skilled in the art recognize that various modifications may be made to the invention without departing from the spirit and scope thereof.

What is claimed is:

1. A method of treating an osteolytic lesion comprising:
   accessing the osteolytic lesion located at an interface between a patient's bone and an orthopedic prosthetic by inserting a cannula or guidewire through the skin and soft tissue, and dilating the soft tissue with the cannula to provide access to the osteolytic lesion, wherein the osteolytic lesion is caused by particulate induced bone resorption;
   preparing the osteolytic lesion for receiving a bone growth promoting substance by debriding a surface of the osteolytic lesion using a debriding device; and
   delivering the bone growth promoting substance to the osteolytic lesion via a delivery apparatus selected from a cannula or graft syringe, wherein the bone growth promoting substance is capable of adhering to the osteolytic lesion and comprises: a carrier and at least one or more osteoinductive agents selected from the group consisting of one or more BMPs, one or more VEGFs, one or more CTGFs, osteoprotegerin, one or more TGF-betas, and any combination thereof.

2. The method of claim 1, wherein the one or more osteoinductive agents are selected from the group consisting of CTGF-1, CTGF-2, CGTF-3, CTGF-4, and any combination thereof.

3. The method of claim 1, wherein the one or more osteoinductive agents are selected from the group consisting of VEGF-A, VEGF-B, VEGF-C, VEGF-D, VEGF-E, and any combination thereof.

4. The method of claim 1, wherein the one or more osteoinductive agents is osteoprotegerin.

5. The method of claim 1, wherein the one or more osteoinductive agents are selected from the group consisting of TGF-.beta.-1, TGF-.beta.-2, TGF-.beta.-3, and any combination thereof.

6. The method of claim 1, wherein the one or more osteoinductive agents comprise BMP-2 and are provided as therapeutic polynucleotides.

7. A method of treating an osteolytic lesion comprising:
   accessing the osteolytic lesion located at an interface between a patient's bone and an orthopedic prosthetic by inserting a cannula or guidewire the skin and soft tissue, and dilating the soft tissue with the cannula to provide access to the osteolytic lesion, wherein the osteolytic lesion is caused by particulate induced bone resorption;
   preparing the osteolytic lesion for receiving a bone growth promoting substance by debriding a surface of the osteolytic lesion using a debriding device; and
   delivering the bone growth promoting substance to the osteolytic lesion, wherein the bone growth promoting substance is capable of adhering to the osteolytic lesion and comprises a carrier and osteoprotegerin.

* * * * *

UNITED STATES PATENT AND TRADEMARK OFFICE
CERTIFICATE OF CORRECTION

PATENT NO. : 8,137,664 B2  
APPLICATION NO. : 11/048064  
DATED : March 20, 2012  
INVENTOR(S) : Nycz et al.

Page 1 of 1

It is certified that error appears in the above-identified patent and that said Letters Patent is hereby corrected as shown below:

In Column 1, Line 31, delete "acetabluar" and insert -- acetabular --, therefor.

In Column 3, Line 26, delete "though" and insert -- through --, therefor.

In Column 3, Line 38, delete "DESCRIPTION" and insert -- DETAILED DESCRIPTION --, therefor.

In Column 6, Line 8, delete "ronguers," and insert -- rongeurs, --, therefor.

In Column 7, Line 14, delete "osteocunductive" and insert -- osteoconductive --, therefor.

In Column 13, Line 21, delete "(trangenic" and insert -- (transgenic --, therefor.

In Column 17, Line 43, delete "rheumatiod" and insert -- rheumatoid --, therefor.

In Column 18, Line 36, in Claim 2, delete "CGTF" and insert -- CTGF --, therefor.

In Column 18, Line 53, in Claim 7, delete "guidewire the" and insert -- guidewire through the --, therefor.

Signed and Sealed this
Eighth Day of May, 2012

David J. Kappos
*Director of the United States Patent and Trademark Office*